(12) United States Patent
Haueter et al.

(10) Patent No.: US 7,931,613 B2
(45) Date of Patent: *Apr. 26, 2011

(54) MODULE FOR A COMPUTER INTERFACE

(75) Inventors: Ulrich Haueter, Grosshoechstetten (CH); Erich Imhof, Utzenstorf (CH)

(73) Assignee: Roche Diagnostics International AG, Steinhausen (CH)

( * ) Notice: Subject to any disclaimer, the term of this patent is extended or adjusted under 35 U.S.C. 154(b) by 819 days.

This patent is subject to a terminal disclaimer.

(21) Appl. No.: 10/919,030

(22) Filed: Aug. 16, 2004

(65) Prior Publication Data

US 2005/0033148 A1 Feb. 10, 2005

Related U.S. Application Data

(63) Continuation of application No. 09/801,276, filed on Mar. 7, 2001, now Pat. No. 6,780,156, which is a continuation of application No. PCT/CH99/00416, filed on Sep. 7, 1999.

(30) Foreign Application Priority Data

Sep. 8, 1998 (DE) .................................. 198 40 965

(51) Int. Cl.
*A61M 31/00* (2006.01)
*A61B 8/14* (2006.01)

(52) U.S. Cl. ................... 604/66; 604/890.1; 604/891.1; 600/459; 600/365

(58) Field of Classification Search ............. 604/65–67, 604/890.1, 891.1, 131, 132, 151, 133–136, 604/140, 118, 121, 150, 154, 156, 246, 247; 600/459, 365, 347, 345, 348, 350; 607/62

See application file for complete search history.

(56) References Cited

U.S. PATENT DOCUMENTS

| | | | | |
|---|---|---|---|---|
| 3,728,574 A | * | 4/1973 | Benda | 313/337 |
| 4,256,437 A | * | 3/1981 | Brown | 417/45 |
| 4,270,532 A | | 6/1981 | Franetzki et al. | |
| 4,372,413 A | * | 2/1983 | Petersen et al. | 180/432 |
| 4,494,950 A | | 1/1985 | Fischell | |
| 4,543,955 A | | 10/1985 | Scroeppel | |
| 4,637,403 A | | 1/1987 | Garcia et al. | |
| 4,871,351 A | * | 10/1989 | Feingold | 604/66 |
| 4,898,578 A | * | 2/1990 | Rubalcaba, Jr. | 604/66 |
| 5,113,869 A | | 5/1992 | Nappholz et al. | |
| 5,232,449 A | * | 8/1993 | Stern et al. | 604/154 |
| 5,376,070 A | * | 12/1994 | Purvis et al. | 604/31 |
| 5,429,602 A | * | 7/1995 | Hauser | 604/65 |
| 5,485,408 A | * | 1/1996 | Blomquist | 703/9 |
| 5,507,288 A | * | 4/1996 | Bocker et al. | 600/322 |
| 5,558,640 A | * | 9/1996 | Pfeiler et al. | 604/67 |
| 5,616,124 A | * | 4/1997 | Hague et al. | 604/65 |

(Continued)

FOREIGN PATENT DOCUMENTS

EP 98592 1/1984

(Continued)

*Primary Examiner* — Nicholas D Lucchesi
*Assistant Examiner* — Quynh-Nhu H Vu
(74) *Attorney, Agent, or Firm* — Dinsmore & Shohl LLP

(57) ABSTRACT

The present invention provides a module for a computer interface including a transducer wherein the transducer receives a measurement value and makes this measurement value available for monitoring an individual's health by means of the computer interface, for example, for monitoring an individual's blood glucose level, wherein the measurement value is obtained by means of a sensor.

32 Claims, 4 Drawing Sheets

U.S. PATENT DOCUMENTS

| | | | |
|---|---|---|---|
| 5,647,853 A * | 7/1997 | Feldmann et al. | 604/155 |
| 5,660,163 A | 8/1997 | Schulman et al. | |
| 5,665,065 A * | 9/1997 | Colman et al. | 604/66 |
| 5,695,623 A | 12/1997 | Michel et al. | |
| 5,711,861 A | 1/1998 | Ward et al. | |
| 5,758,643 A | 6/1998 | Wong et al. | |
| 5,772,586 A * | 6/1998 | Heinonen et al. | 600/300 |
| 5,772,635 A * | 6/1998 | Dastur et al. | 604/131 |
| 5,776,324 A | 7/1998 | Usala | |
| 5,791,344 A * | 8/1998 | Schulman et al. | 600/347 |
| 5,795,327 A * | 8/1998 | Wilson et al. | 604/65 |
| 5,807,336 A | 9/1998 | Russo et al. | |
| 5,840,020 A | 11/1998 | Heinonen et al. | |
| 5,844,862 A | 12/1998 | Cocatre-Zilgien | |
| 5,885,245 A | 3/1999 | Lynch et al. | |
| 5,895,371 A | 4/1999 | Levitas et al. | |
| 5,959,529 A * | 9/1999 | Kail, IV | 340/539.12 |
| 5,960,403 A * | 9/1999 | Brown | 705/2 |
| 5,961,451 A * | 10/1999 | Reber et al. | 600/322 |
| 6,159,147 A | 12/2000 | Lichter et al. | |
| 6,246,992 B1 * | 6/2001 | Brown | 705/2 |
| 6,269,340 B1 * | 7/2001 | Ford et al. | 705/3 |
| 6,295,506 B1 * | 9/2001 | Heinonen et al. | 702/104 |
| 6,379,301 B1 * | 4/2002 | Worthington et al. | 600/309 |
| 6,554,798 B1 * | 4/2003 | Mann et al. | 604/131 |
| 6,558,320 B1 * | 5/2003 | Causey et al. | 600/300 |
| 6,641,533 B2 | 11/2003 | Causey et al. | |
| 6,699,188 B2 * | 3/2004 | Wessel | 600/300 |
| 6,780,156 B2 * | 8/2004 | Haueter et al. | 600/459 |
| 2008/0234663 A1 * | 9/2008 | Yodfat et al. | 604/890.1 |

FOREIGN PATENT DOCUMENTS

| | | |
|---|---|---|
| EP | 0777123 A2 | 6/1997 |
| GB | 1574267 | 9/1980 |
| GB | 2153081 | 8/1985 |
| GB | 2311886 A | 10/1997 |
| WO | WO 95/28878 | 11/1995 |
| WO | WO 97/08544 | 6/1997 |

* cited by examiner

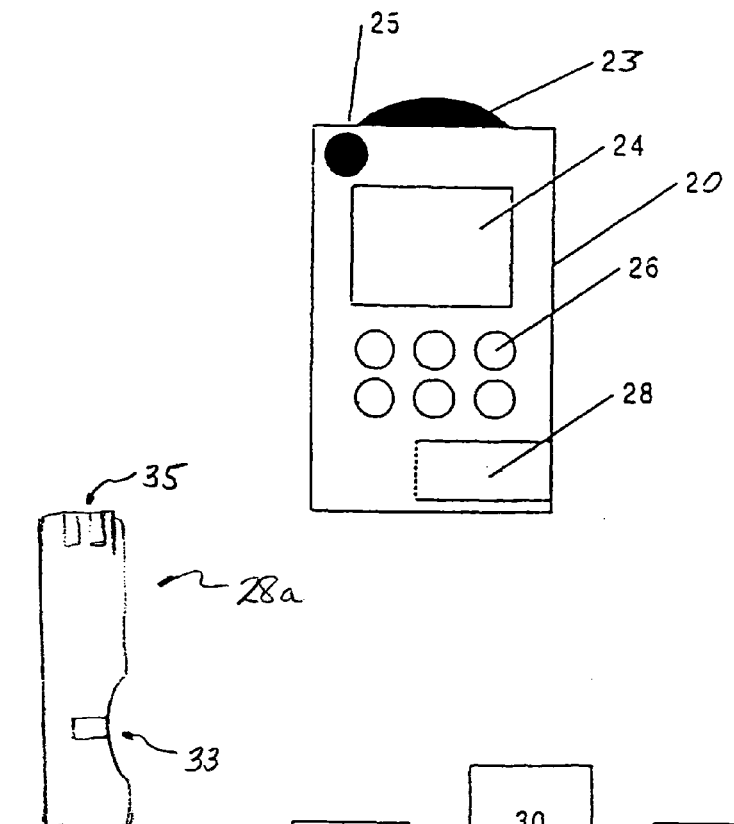
Fig. 2
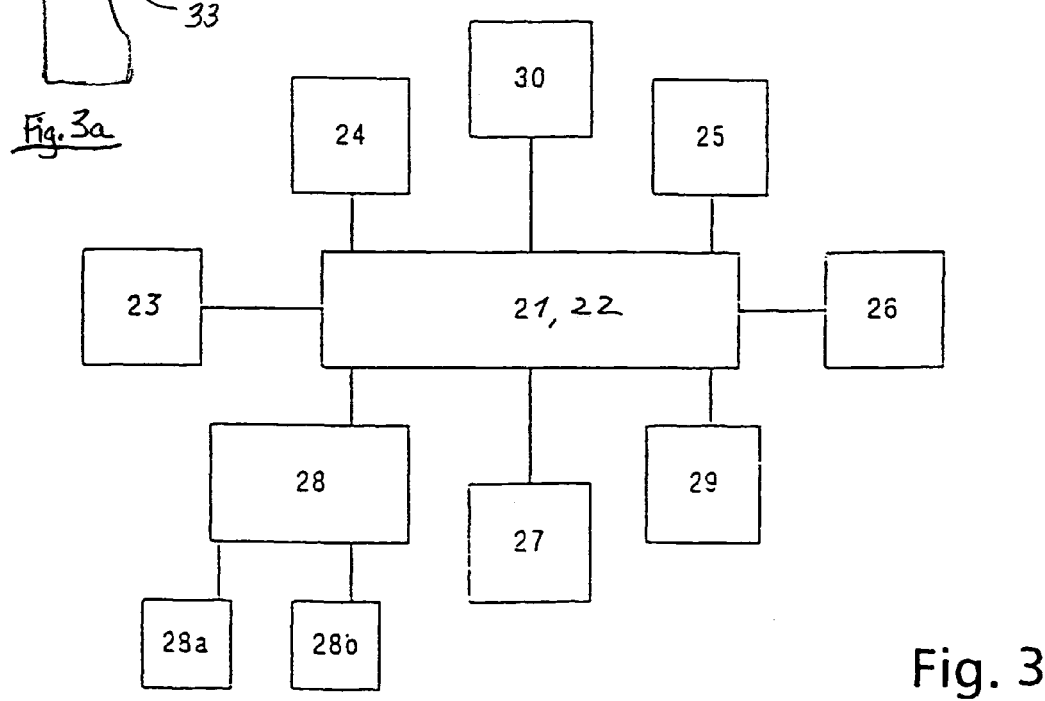
Fig. 3a
Fig. 3

MODULE FOR A COMPUTER INTERFACE

RELATED APPLICATIONS

This application is a continuation of U.S. patent application Ser. No. 09/801,276, filed Mar. 7, 2001, which claims priority from international application number PCT/CH99/00416, filed Sep. 7, 1999, which claims priority from German patent application number 198 40 965.6, filed Sep. 8, 1998, all of which are incorporated herein by reference.

BACKGROUND

The invention relates to a module for a computer interface, the module being used to monitor the state of health of a person. More particularly, the present invention provides an apparatus for and a method of health monitoring and control wherein a module for a computer interface including a transducer wherein the transducer receives a measurement value and makes this measurement value available for monitoring an individual's health by means of the computer interface, for example, for monitoring an individual's blood glucose level, wherein the measurement value is obtained by means of a sensor.

Monitoring the state of health of persons has become increasingly important. This particularly applies to the execution of therapies requiring a dosed administration of one or more active substances depending on the state of health of the person concerned. Such a therapy may be, for example, diabetes therapy, where insulin is administered in synchronization with the glucose concentration measured or detected by measurement in and/or of a body fluid of the person.

The monitoring methods in the context of therapies require special devices just for the purpose of making measurement data available either to care-givers such as doctors, nurses, etc. or to the person to be treated. Such monitoring devices are complex and expensive or only allow monitoring activities to a very restricted extent. In diabetes therapy, where the glucose concentration in a body fluid, particularly the blood-sugar content, is decisive, the known devices for monitoring the glucose concentration just indicate the currently measured concentration. Evaluating and monitoring features are at least very limited. A user who administers himself with insulin, or with the corresponding active substance in another therapy, would be able to adapt this administration to his personal requirements more precisely if, for example, "historical" data were also available to him. He could coordinate his physical activities, eating habits and the doses of active substances to be administered more precisely.

SUMMARY

Accordingly, it is the object of the invention to enable a comfortable, inexpensive, and yet extensive, monitoring of the state of health of a person.

This object is solved by the invention in that a transducer, which receives or takes a measurement value and makes it available for monitoring the state of health of a person, has been designed as a module for an interface of a conventional computer. The measurement value is a value obtained by means of a sensor on or in the person to detect his/her state of health. The module can be integrated and connected to a defined interface of the computer. Accordingly, not only can it be supplied by computer manufacturers, but also by independent manufacturers at a later time.

In one embodiment, the module according to the invention is used to monitor the glucose concentration in a body fluid of the person, in particular to monitor the blood-sugar content.

An advantage of the present invention is that monitoring can be done by conventional computers that generally offer a higher performance, in particular with regard to the computing performance and display features, than so far possible with special devices used for monitoring purposes. Another advantage is that, especially in types of therapy requiring a person to administer himself with the corresponding active substance, this person can make use of a computer generally already available, which he already uses for other purposes and is already familiar with. It is also possible to transmit data concerning health from the module in accordance with the invention to other, widely used computer programs. The module in accordance with the invention or its computer software is compatible with the usual programs, such as, for instance, graphic, text and/or spread sheet programs. In one embodiment, the module in accordance with the invention is a plug-in module that may be advantageously inserted into a standard slot of a computer, such as, for example, in the form of the standard plug-in board or cards usual today for an external port of a computer. It can also be a plug-in module subsequently integrated into one of the slots available in the housing of a personal computer. In any case, the computer's capacity is used. In particular, processor and monitor capacities, but also possibilities already available to connect peripheral devices can be exploited by the invention. Accordingly, to monitor his state of health, the user can make use of the computer surroundings he is already familiar with, which increases the readiness to accept such monitoring. Preferably, such a plug-in module is delivered together with the corresponding installation and application software required for monitoring, as is common with add-on plug-in modules.

The invention may be used with a computer of a device used for self-administration of a fluid product or with a computer used in combination therewith. The device comprises a fluid guiding means, a means for conveying a dose of fluid product to be administered, a wireless communication interface, a control for the conveying means, and a communications terminal. The fluid guiding means, conveying means and said interface are components of an administering device. The communications terminal is not physically connected to said device, i.e., these two devices are not mechanically connected to each other, at least when using the device. Any connection while stored or during transportation should, however, not be ruled out. The communications terminal is provided with another interface for wireless communication and with a visual display. Wireless communication occurs between the administration device and the communications terminal via these two interfaces. The administration device and the communications terminal remain with the user, who administers the fluid product to himself personally.

The fluid guiding means includes a reservoir for the fluid product and for the parts of the administration device connected therewith, and fluid passes through the guiding means during administration until a fluid outlet is reached. In the event that the administration device is fixed either to the body or to clothing, the fluid outlet is formed by a insertion needle.

In another embodiment, the conveying means, an emergency control therefor, an energy source and the wireless communication interface are implanted, and the reservoir is fixed either to the body or to the clothing, the fluid guiding means naturally also being partially implanted downstream of the reservoir; the conveying means, preferably a micro pump, is itself thus preferably part of said fluid guiding system. This is generally also possible for the other alternative embodiments with regard to the design of the administration device. Dividing the administration device into a body-external reservoir and a body-internal conveying means has the advantage that the external part can be diminished or the reservoir can be enlarged, and that the place of discharge of the fluid product can be selected particularly conveniently for therapy. At the same time, the health risks associated with an implanted reservoir are avoided.

The fluid product may be a liquid active solution as administered in the context or framework of a therapy, in particular insulin.

The wireless communication may be radio communication; however, ultrasonic or infrared communication is also conceivable.

The communications terminal monitor displays at least one operating parameter of the administration device. Thus, a person administering himself with the fluid product can monitor the operation of the administration device, and thus the administration, directly and comfortably by means of the communications terminal. The user does not have to detach the administration device to read the display, as he can read the data of interest to him on the display of the communications terminal which is already detached, irrespective of the place where the administration device has been attached. Accordingly, the administration device can be fixed at any suitable place, e.g., to the user's clothing or directly to the user's body for an administration cycle until the reservoir is filled again. Thus, carrying the device becomes much more comfortable for the user. The administration device can be constantly positioned under clothing, for example under a pull-over, so that it is invisible to other persons, which renders the device much more acceptable. The facilitated readability simultaneously increases safety, amongst other things, since the user checks the display more often. Further display means can be provided at the administration device, but are no longer required, and are preferably not, or only to a reduced extent, available at the device.

One operating parameter of the administration device which is of interest to the user is the amount of fluid administered. In the course of a continuous or almost continuous product distribution, the amount of fluid is preferably displayed as feed rate over time. In particular, the fluid amounts supplied in discrete time intervals are displayed, the time intervals either being given or selectable with regard to the therapy and, if desired, also with regard to the individual user requirements.

The amount of fluid administered during a given time interval is preferably determined from the position of the conveying means. Comparing a position at the end of a time interval to a known starting position at the beginning of said time interval calculates the amount of fluid supplied during the respective time interval, i.e., by subtraction and scaling the fluid reservoir. Storing the positions passed or the supplied amounts detected during administration allows or translates to representing the amount of fluid administered over the time. Such a representation is preferably a graphic representation. To increase the safety of administration, any deviation from a given desired position may also be represented, for example also over the time of administration. In case the deviation from a given desired position is too large, it would be advantageous to display a warning signal to signalize to the user that there is a considerable deviation, or even to indicate the extent of deviation and, expediently, also the moment when such a deviation occurred. Furthermore, it can also be beneficial to display the course of time of such deviation between the desired amount of supply and the amount of fluid actually supplied. The position of the conveying means preferably also allows to determine the residual amount of fluid product still available, since each position is directly assigned a given residual amount when the fluid reservoir does not change in form and size, i.e. if, for example, ampoules of same size are always used or if changes are recognized automatically or manually entered at the communications terminal.

The position of the conveying means can be a desired position given by a control for controlling the conveying means precisely to said position. According to another embodiment, the actual position of the conveying means obtained by a sensor is used to determine the amount supplied and the further operating parameters that can be derived therefrom.

In a one embodiment, the fluid guiding means is monitored with regard to an occlusion. The communications terminal indicates the occurrence of an occlusion and preferably the extent thereof. An occlusion can either cause total interruption of the supply or a supply at reduced supply rate. In case of total interruption, the conveying means is automatically stopped and the total interruption is indicated by an alarm signal at the communications terminal. If the supply is continued despite an occlusion, the actual supply rate is just smaller than a given supply rate, and if this interruption in operation is due to an occlusion in the fluid conveying system, this may be indicated on the communications terminal visual display, especially by means of a graphical warning symbol and, simultaneously, by a suitable representation of the deviation occurred. In the event of a deviation due to a conveying error caused by the conveying means, the user can directly compensate the conveying error at the next opportunity to do so. A total occlusion may be stored as an event in a memory of the communications terminal together with the time of detection. In the event of a reduced supply, the extent of which can be determined due to the position of the conveying means, it is stored over its course of time. As already stated above, it is possible to represent either the amounts of supply or the supply rate in absolute form, or the deviation from the desired supply. In another embodiment, a leakage in the fluid guiding system may be detected and sent to the communications terminal, where it is indicated by an alarm signal. The leakage information may be stored as an event in a memory of the communications terminal together with the time of detection so that it is available for later evaluation of the course of administration.

The occurrence of an occlusion may be detected by means of a sensor that measures a reaction force the conveying means exerts on a support of said conveying means. The measured reaction force is constantly compared to a suitably given threshold value, which when exceeded indicates an occlusion. The same sensor may also be used to detect a leakage. The measured reaction force is then additionally compared to a suitably given threshold value. If the measured force of reaction remains under such a threshold value, this indicates a leakage.

A means to produce a defined pressure drop is preferably provided in a flow cross section of the fluid guiding system. The pressure drop is of such large dimension that the force required for the conveying means to overcome this flow resistance is considerably larger than the other forces determining the reaction force occurring if the administration device works properly. Accordingly, an occlusion, and in particular a leakage, can be detected with particular reliability.

A communications terminal, which may be, at the same time, a remote indicator and remote control, offers the most conceivable convenience as concerns portability. Owing to the remote control, a user cannot only monitor, but also use, his administration device discretely, should this be required, e.g., in a restaurant or at any other social event. Data can be entered into the communications terminal by means of keys, a touch screen or a voice-entry means with integrated microphone, the latter may also be provided in addition to a manually operable input means to enable data to be entered in all situations with utmost convenience and discretion.

The physical size used to determine the at least one operating parameter, preferably the position of the conveying means and/or the reaction force exerted by said conveying means, is entered into a processor of the device to generate the operating parameter therefrom. If said processor is a component of the administration device, the operating parameter generated by said processor is entered into the interface of said administration device and then further transmitted to the interface of the communications terminal. Preferably, such a processor is a component of the communications terminal, and the physical size is transmitted.

A control for the conveying means, which can be influenced or operated by the user, can be a component of the administration device. The user can change the setting of such a control by means of an input means of the communications terminal, e.g., to administer an extra dose.

In one embodiment, a control that can be influenced, in particular a programmable control or the entire variable part of the control of the conveying means, is a component of the communications terminal. Provided in the administration device is a part of the control, which can only be provided directly at the conveying means, if need be a wireless controlled power component of said conveying means, e.g., in the form of just one pulsed interrupter of the energy supply of said conveying means.

If the communications terminal comprises the variable control part, the administration device may include a an emergency control used to further run a fixed administration program automatically and self-sufficiently in the event of the wireless communication failing until it is switched off. The emergency control can be provided in addition to the wireless triggered minimum control part of the main control. It can, however, also be formed by the wireless-controlled control means in the course of normal operation that switches to emergency operation if no control signals are obtained within a given period of time. The emergency control can operate in accordance with a standard program, which is the same for all administration devices of the same series, or is also adjusted individually, preferably by means of programming which, according to the setting of the user, is carried out in a wireless manner via the interface of the administration device by means of the communications terminal or any other suitable device, which is conventionally done by a doctor. In some embodiments, it does not include further adjusting features, but rather runs the standard or individual program once set.

The administration device can easily be designed waterproof, since a housing has few openings, e.g., for input means. In extreme cases, only the interface region and the outlet for the fluid guiding means must be sealed.

According to one embodiment, an evaluation means for monitoring the state of health of a person, in particular of the user of the device, can be combined with the communications terminal or is a fixedly integrated component thereof. The evaluation means may be a component of the module according to the invention.

An obtained measurement value is evaluated by the evaluation means by determining a corresponding body value therefrom. An evaluation result may be indicated on another monitor or preferably the monitor of the communications terminal, already mentioned. If the device according to the invention is used for insulin treatment, it may be an evaluation means used to determine the blood-sugar content; it can also be used to additionally determine the hormone level and/or a relevant body temperature. Generally, however, such an evaluation means is not restricted to determine blood-sugar measurement values or the measurement values and groups of measurement values previously mentioned. If used for other therapies, where not insulin but other active substances are being administered, other measurement values adapted to the corresponding application would be obtained and evaluated.

The measurement value can be transmitted wirelessly as a measuring signal by a sensor. The evaluation means comprises a transducer to receive said signal. In this embodiment, the transducer is either formed by the interface of the communications terminal or as an additional receiving part. In another embodiment, a sensor, which is or was in contact with the sample, is inserted into the transducer in its contact area, which thereby obtains the measuring signal of the sensor by direct contact. In both cases, the transducer is the link between the sensor and the communications terminal or another platform for the evaluation means.

In the embodiment including the sensor, which has to be introduced physically, the sensor and the evaluation means may correspond to sensors and evaluation means known from insulin therapy. However, in contrast thereto, the evaluation means according to the invention is compatible with the communications terminal or a common computer, which is, however, adapted to the application.

According to the invention, the transducer is an integrated component of the module, in particular a standard plug-in board or card for computers, e.g. a PCMCIA board or card, and can thus be connected to usual well-known types of computers such as personal computers, notebooks and pocket-sized computers by simply being plugged into a computer slot provided for this purpose. The plug-in board or card may be thought of as a transducer, i.e., as a transmitting means for the measurement values of the sensor. The subsequent processing of the measurement values until the body values are obtained can be performed by components comprised in the home computer. In this embodiment, the plug-in board or card may be thought of as a sensor port. In another embodiment, means used to process the measurement values is also an integrated part of the board or card. The board or card may include a non-volatile memory to temporarily store the measurement values or the measurement values already processed. The plug-in board or card can be delivered with a preinstalled or installable special application software.

The plug-in board or card may include an integrated sample taking set comprising a number of sensor elements and means to take samples. Alternatively, such a sample taking set can also be a component of the communications terminal, in particular if the evaluation means is an integrated component of the communications terminal.

In one embodiment, the communications terminal is a standard computer in pocket format, e.g., a hand-held or preferably a palm-sized computer. The interface of the communications terminal for wireless communication with the administration device is formed by a plug-in board or card, e.g., a PCMCIA board or card, for a computer slot. The same plug-in board or card may include the transducer that may be designed with additional components on the board or card up to an evaluation means, thus simultaneously forming the communication interface and sensor port.

The integration of an evaluation means or also only a transducer in one module, preferably in a plug-in module, in particular a plug-in board or card, may advantageously also be applied in combination with administration devices that do not have a detached communications terminal. Such a modular solution can advantageously be used for any therapy monitoring in order employ larger calculating and storing capacities, in comparison to known devices, and also more extensive display possibilities of a computer. As a plug-in module, this solution may be a product that can be sold independently.

Configuration, diagnosis or quality control, and programming or pre-setting of the administration device may be done by the manufacturer in a wireless manner by means of a computer. In particular, the wireless communication facilitates execution of quality checks. As this does not require any wire connections, configuration and diagnosis may be performed without interrupting production if an interface for wireless communication is suitably provided.

Additional features and advantages of the present invention will be provided by references to the accompanying drawings, the following description and the appended claims.

BRIEF DESCRIPTION OF THE DRAWINGS

A preferred embodiment of the invention will be explained in the following by means of the following figures, in which:

FIG. 2 is a view of the communications terminal;

FIG. 3 is a block diagram of the communications terminal;

FIG. 3a depicts an exemplary embodiment of a commonly used sensor;

DETAILED DESCRIPTION

Figure 1:
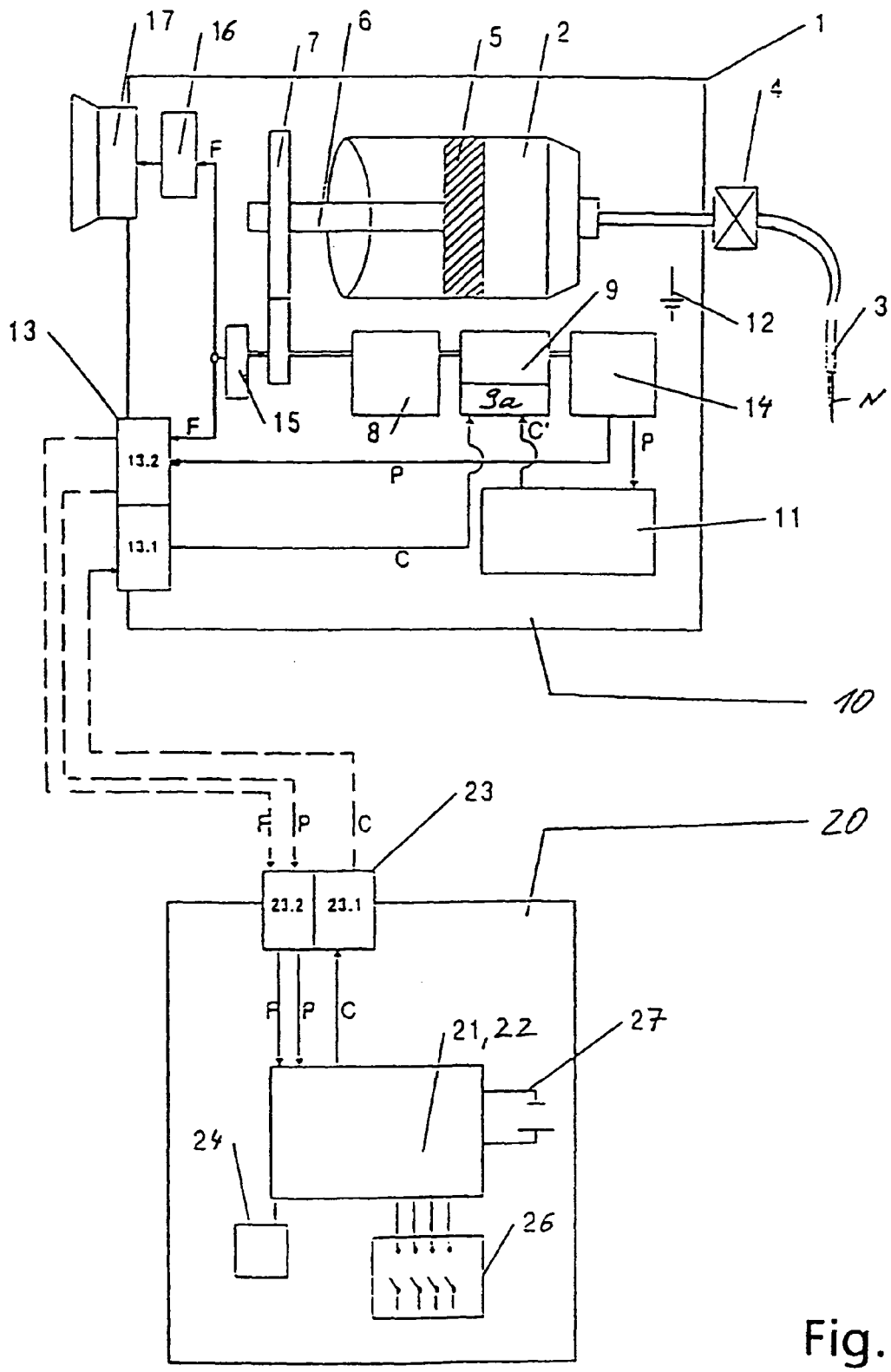
FIG. 1 is a device for self-administration of a fluid product with a communications terminal for wireless communication.

FIG. 1 shows an administration device 10 in the form of an infusion pump for insulin that is in wireless communication with a communications terminal 20. The administration device 10 comprises a housing 1, provided with suitable holding means, to enable it to be either secured by the user to his clothing or directly to his body so that it may be constantly carried around.

The insulin is contained in a reservoir, which in the example embodiment is formed by an ampoule 2. A piston 5 is shiftably accommodated in said ampoule 2. Displacement of the piston 5 occurs by means of a spindle drive, the driven member 6 of which (a threaded rod in this embodiment) is straightly and axially moved with regard to the housing 1 by means of the rotary drive of a drive member 7, which in this embodiment is a threaded sleeve. The rotary drive of the threaded sleeve 7 is caused by a stepper motor 9 via a gear 8 with a spur wheel meshing with said threaded sleeve 7. A power part of a control for the motor 9 is given reference number 9a. By means of rotation-secured, straight guidance of the threaded rod 6 in the housing 1, the threaded rod 6 is axially moved and urged against the rear of the piston. Under the action of the threaded rod 6, the piston 5 is moved to an ampoule outlet, thereby displacing insulin through said ampoule outlet. A fluid line 3 is connected to said ampoule outlet, at the free front ends of which an infusion needle N is fixed, which the user pierces under his skin and then fixes it on his skin so that he can self-administer insulin.

Further included in the fluid line 3 is a valve 4, likewise accommodated in the housing 1, which only enables insulin to flow when a minimum pressure, given by said valve 4, is exceeded in said ampoule 2.

A position sensor 14 measures the actual value of the angular position of the stepper motor 9 and transmits it via signal lines as the actual position P to a radio interface 13 and to an emergency control 11 provided in the housing 1.

If run properly, the emergency control 11 is driven in a stand-by mode. The emergency control 11 is connected to the position sensor 14 and the power element 9a via signal lines. It receives the actual position P from the position sensor 14 and transmits its adjusting signal C' to the power element 9a, if the emergency control 11 has been activated, to move the motor 9 to a subsequent desired position. An electric battery, provided in the housing 1, is the energy source 12 for the energy-consuming components of the administration device 10.

A reaction force F, exerted by the piston 5 on the housing 1, is constantly measured by an energy sensor 15 and outputted in the form of a measurement signal representing the measured reaction force F. The measured reaction force F is supplied to said radio interface 13 and a threshold comparator 16 via signal lines, the comparator triggering an acoustic alarm of an alarm means 17 when a given upper threshold value for the measured reaction force F has been exceeded or when a given lower threshold value of said force has been fallen short of. The energy sensor 15, the comparator 16 and the alarm means 17 form a device to trigger an emergency alarm.

The entire driving mechanism of the piston 5, namely, the spindle drive comprising driven member 6 and drive member 7, gear 8, motor 9 with power element 9a, along with the position sensor 14 as well as the emergency control 11, are together shiftably positioned on a straightly guided platform in the housing 1 in and against the advancement direction of the piston 5. Arrangement of the platform occurs in and against the advancement direction of the piston 5 in a free-floating manner. The energy sensor 15, e.g., a suitably arranged wire strain gauge, is arranged at an underside of the platform or opposite to the housing 1 so that it outputs a measurement signal when the platform and the housing 1 are urged together, this measurement signal representing the acting force. This force corresponds to the reaction force F exerted by the piston 5 on the threaded rod 6 and thus on the platform.

Via the radio interface 13, there is wireless communication between the administration device 10 and the communications terminal 20, which has been designed in the embodiment as an integrated remote indicator and control unit, and is provided with a radio interface 23.

Both radio interfaces 13 and 23 are each provided with a receiving member 13.1 or 23.1 and with a transmitting member 13.2 or 23.2. The administration device 10 permanently or periodically transmits those values of the measured reaction force F and the actual position P via transmitter 13.2 that are received by the receiving member 23.1 and are transmitted via signal lines to a microprocessor 21.

From the actual position P, the processor particularly determines the supplied basal rate, preferably in insulin units per hour IU/h, dose amounts in insulin units IU as well as the filling state of the ampoule 2 and/or the actually remaining residual amount IUR and/or the presumed residual feed time. The determined basal rate and the dose amounts are stored. The reaction force F is compared by the microprocessor to a given upper threshold value for this force. Exceeding the upper threshold value determines the occurrence of an occlusion in the fluid guiding system, which is stored together with its moment of occurrence. By determining a lower threshold value and comparison therewith, a leakage in the fluid guidance system can be detected and its time of occurrence can be stored.

At the same time, processor 21 forms a variable control 22 for the motor 9 in normal operation, in which the emergency control 11 remains in its stand-by mode. The control function will be taken over by the emergency control 11 instead of the processor control 21 if there is an emergency case such as a communication error or any other detected control error leading to a loss of control signals. Otherwise, the motor is controlled by the processor control 22 via wireless transmission of its adjusting signals C.

FIG. 2 is a front view of the communications terminal 20. All components of the communications terminal 20 are included in a lightweight housing that can be held in a person's hand. The measurement signals P and F as well as the adjusting signals C are exchanged via interface 23 by interface 13. A visual display 24 displays information of relevance to the user. Indicated data or data that can be indicated upon request in a display mode are at least operating parameters of the administration device 10. Readability of data, especially in the case of continuously performed administration, has considerably been improved by means of the remote indicator, which can also be comfortably hand-held. The variety and complexity of the indicated information can be increased without having to increase the weight and the dimensions of the administration device.

The operation of the device has been further improved in that the communications terminal 20 has not only been designed as a remote display, but also as a remote control. In this connection, the terminal 20 is provided with input means 26 in the form of keys used to act upon the processor 21, and thus also on control 22 formed by the processor. For example, pressing a key can cause a bole output, which is either spontaneous or programmed in advance in a delayed manner depending on the input. The visual display 24 and keys 26 may also cooperate by indicating on said display 24, for example, key settings or data that can be selected via keys 26. Furthermore, the communications terminal 20 comprises an acoustic alarm indicator 25, which acoustically alerts one to dangerous malfunctions of the communications terminal 20 and also of the administration device 10.

As concerns the operational function, the administration device 10 can be switched on or off by means of the communications terminal 20 and a dose supply can be activated or at least increased or reduced. Furthermore, the basal rate and the temporary basal rate can be set and preferably also changed. Filling the catheter after replacement of the ampoule can also be done in such a controlled manner.

According to FIG. 3, the essential components of the communications terminal 20 are linked to each other and depicted in the form of a block diagram. The microprocessor 21 is the central component and controls both the visual display 24 and the acoustic indicator 25 in response to input signals obtained from the interface 23 or the input means 26. Also indicated is an energy source 27.

The communications terminal 20 is provided with a monitoring means 29 to monitor the position of the stepper motor 9. To do so, it receives the actual position P of the position sensor 14 via the interface 23 together with the desired value from the processor control 22. If a given maximum difference is exceeded in terms of its absolute value, the acoustic alarm 25 delivers an alarm signal. Any deviations that are still tolerable will be indicated and the user can take them into account and compensate for them via the remote control at the next opportunity, e.g., by means of an extra dose supply. No control occurs. In the event of failure of the processor control 22, the comparison between desired/actual values, effected merely for security, can also be performed by the emergency control 11, an intolerable deviation will be indicated by the alarm means 17.

The microprocessor 21 has access to an individual memory 30 of the communications terminal 20, in which in particular a setup of an individual person and the historical administration data are stored or continuously accumulatingly stored. It is further possible to store blood-sugar measurement values over the time, either in an individual area of the memory 30 or in another memory of the communications terminal. This allows the user to compare the administration history to the timely assigned blood-sugar measurement values so that he can draw valuable conclusions therefrom, possibly also for future administrations and individual settings of his administration device. The communications terminal 20 is the user's electronic diary.

A blood-sugar measuring means is likewise integrated into the housing of the communications device. The blood-sugar measuring means comprises a sensor 28a and a transducer 28b. The sensor 28a measures the blood-sugar content of a blood sample and/or a cell fluid sample. The transducer 28b receives a measurement signal outputted from the sensor 28a, the size thereof depending on the blood-sugar content of the sample, and transmits it to the microprocessor 21, i.e. to an evaluation means 28 formed by the microprocessor. The measurement value obtained by the processor is stored in the memory 30 so that it is available for representation on the display 24 at a later time. Referring to FIG. 3a, the sensor 28a is a commonly used sensor, particularly in the form of a strip, having a sample region 33 for applying the sample and a contact region 35 for insertion into the transducer 28b so as to be in contact therewith. The blood-sugar measuring means consists of the sensor 28a, the transducer 28b, used as the receiving and contacting means for the sensor 28a, a connection means for connection to the processor 21, and the processor 21 itself, by which the evaluating function is met if programmed in application-specific manner and which performs in the embodiment all further tasks involved with the evaluation and representation of the measurement signals of the sensor 28a.

The blood-sugar measuring means can either completely, as described above, or partially be designed as an independent module that is inserted into a prepared slot of the communications terminal 20 so as to be connected with the processor 21. If integrated into the detachable module, the evaluation means 28 can be formed by a converter which converts the measurement signal, received from the sensor 28a, into a signal the processor 21 can read. According to another embodiment, the evaluation means 28 itself can store a measurement signal, received from the sensor 28a, in the memory 30 so that it does not have to be stored by the processor 21. Detection of the blood-sugar contents can also be performed by such a transducer and evaluation module. A memory can also be a component of the module to temporarily store therein the measured sensor signals. A measurement means in the basic form of a pure transducer 28b or in one of the above developed forms may advantageously be used for any kind of device, in particular a generic device without operating parameter display, for example, in combination with a pure remote control or a remote display including other displayed data. According to the embodiment in the form of a detachable module, it may advantageously also be (in a basic form or in one of the above developed forms) an independent product that does not depend on a specific device to administer a fluid product. In such a form, it is especially comfortable when used to support any therapy monitored by a user. It can have an own display so that it can be used without a computer like common evaluation means.

Figure 4:
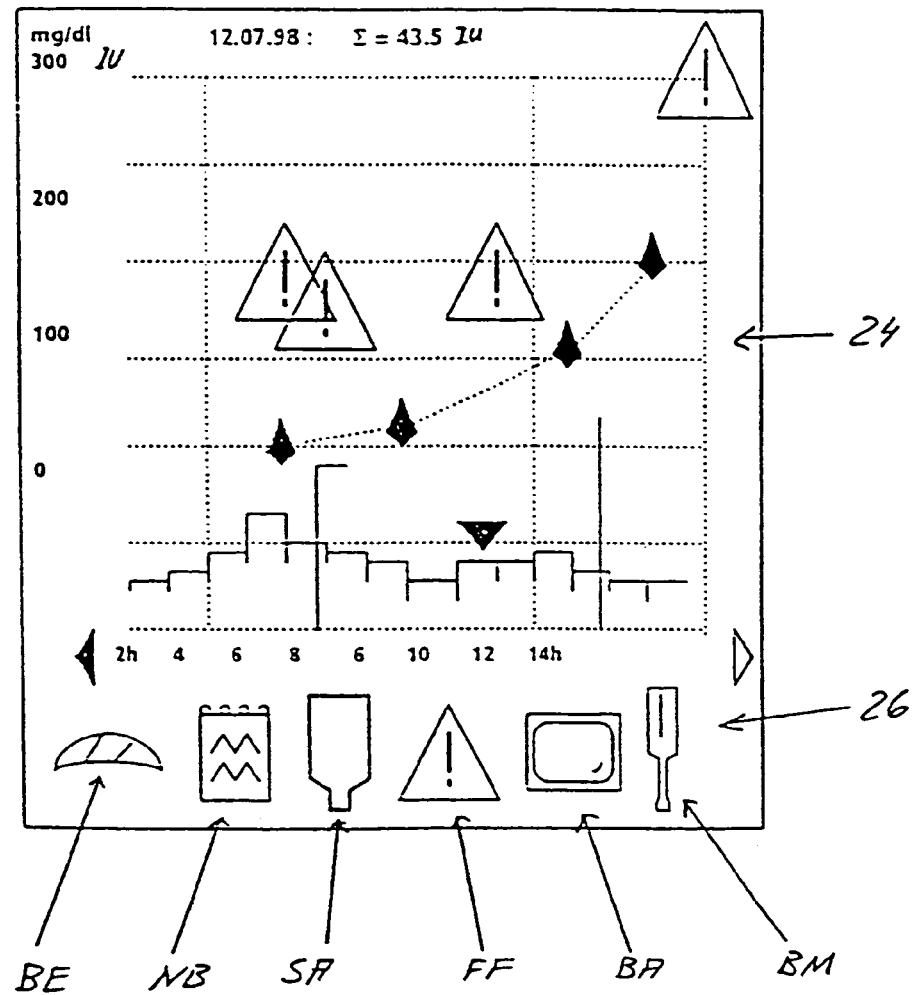
FIG. 4 is a touch-screen display.

FIG. 4 shows a representation as it appears on a touch screen of a palm top computer after selection of a loaded diabetes program. The display is a combined graphic display and input means.

The display permanently, semi-permanently or on demand shows the accumulated amount of insulin administered per hour as basal rate during the last hours in the form of a bar chart in insulin units per hour. Any extra dose supplies, caused by the user, are also permanently shown. A normal dose is represented by a simple vertical line and an extended dose is represented by an above offset line. The amount administered by said dose is indicated by the vertical line length. The time axis indicates the period of the last hours, for example the last 24 hours, with exact time indications. The administered insulin amounts are detected by the processor 21 from actual positions P and stored in the memory 30 so as to be available at any time for display purposes and further evaluation purposes. As long as the monitoring device 29 does not detect a malfunction, the desired positions can be simply taken by the control 21 instead of the actual positions P and be used to determine the delivered insulin amounts. Finally, the total amount of insulin administered during the last 24 hours before reading is permanently shown in the form of its numeric value behind a summation sign.

Under the display area, the display is provided with an input area with input fields 26. Assigned to each of the input fields 26 is a graphic symbol representing the respective function. The meaning of input fields 26 from the left to the right are as follows: bread units BE, notebook NB, status of ampoule SA, malfunctions FF, blood-sugar display BA and blood-sugar measurement BM. Pressing one of these fields activates the function thereof, repeated pressing deactivates the function. Any conceivable combination of fields may be active at a time. FIG. 4 shows the display in a condition in which only fields FF and BA are activated.

Pressing field BE enables the bread units obtained to be entered manually including indications concerning time and amount. Pressing field NB enables the user to input personal notes that are important for him, which will be stored together with the time input by the user or, if the user does not define the time, automatically together with the moment of time the NB field was activated. At the same time, there will be a real-time representation on the display of the bread units or notes input for the indicated period which correspond to the activated input field. Pressing field SA displays the current level of the ampoule in percent of the filling amount of a new ampoule and/or as still remaining residual amount of insulin or as estimated residual feed time. Furthermore, the time of the last ampoule change may also be additionally indicated. Activating field FF suitably indicates a real-time representation of any deviation from the desired operation, e.g. an occlusion, a communication error or a power failure, within the warning symbol. Pressing field BA brings about the display of the blood-sugar contents obtained by measurements, e.g. in milligram of sugar per deciliter of blood at the time of the respective measurement. This time is determined by the user by pressing field BM. Automatic determination of this time would also be conceivable. Other fields may be programmed as well.

Figure 5:
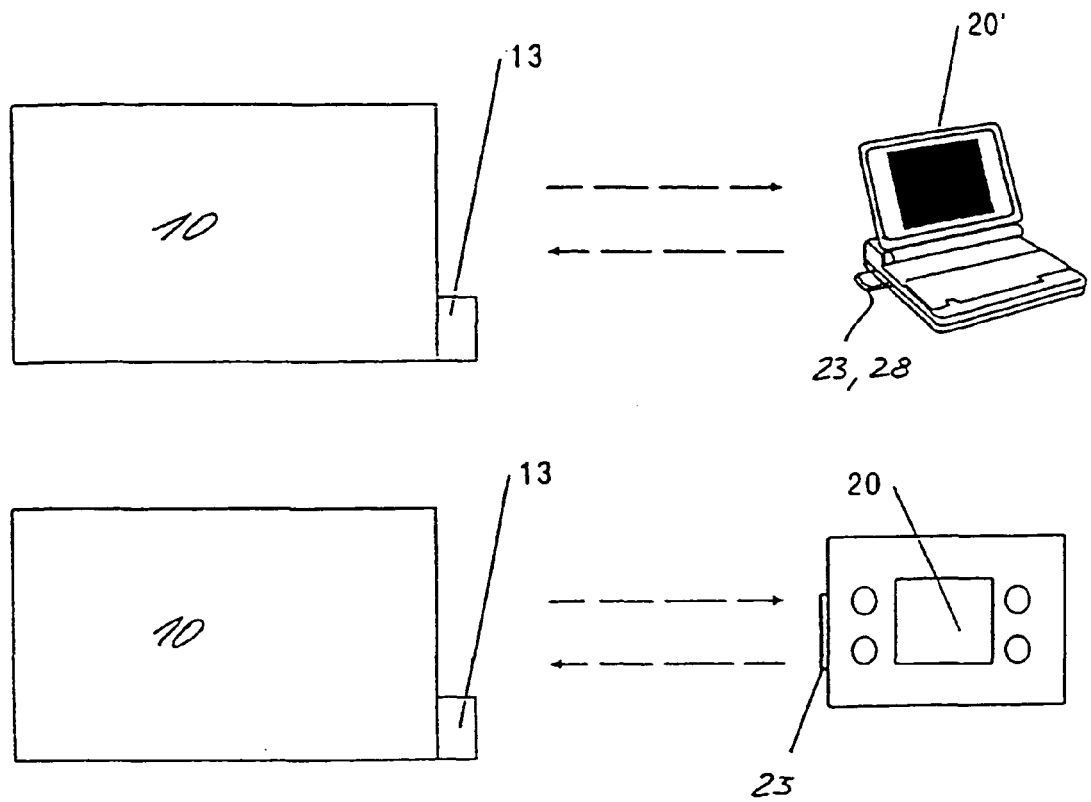
FIG. 5 is a wireless communication between the administration device and two alternative communications terminals.

Represented in FIG. 5, in addition to the wireless communication with the communications terminal 20, is also the possibility of communication with a computer 20' via the same interface 13, it being a notebook in FIG. 5. To use a standard computer 20' equipped with a comparatively large monitor considerably increases the variety and complexity of the applicability of the remote display and the remote control. By means of the personal computer 20', the administration device can be entirely configured and/or programmed, by the manufacturer, with the exception of the settings concerning the individual person. In some embodiments, the individual settings may be preset or programmed as well. In some embodiments, the individual on-spot configuration for the user, and in particular the evaluation possibilities available to the user, e.g., comparing the administration history with the blood-sugar values, can be performed very comfortably and extensively. Wireless communication can also be used by the manufacturer for economical configuration and/or quality control purposes. Particularly with regard to quality control, it is not necessary to establish wire connection between the administration device to be checked and the computer employed for checking purposes. Quality control can be performed by means of wireless communication, for example, or the production line without interrupting production.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:

1. A system for administering a medical fluid to a body and for monitoring a substance level in a bodily fluid, the system comprising:
   an administration device comprising a reservoir adapted to contain the medical fluid, a motor and drive mechanism for displacing the medical fluid from the reservoir into the body, and a first communication interface; and
   a communication terminal remote from the administration device and comprising a housing, a processor, an input device in communication with the processor, a display in communication with the processor, a second communication interface in communication with the processor and configured to communicate with the first communication interface, a measuring device in communication with the processor and comprising a sensor configured to sense the substance level in the bodily fluid, and a memory;
   wherein the processor is operatively associated with the memo and adapted to execute computer implemented instructions to receive communications from the administration device relating to medical fluid amounts delivered from the administration device, and to store in the memory historical medical fluid administration data and substance level measurement values over time based on the communications received from the administration device.

2. The system of claim 1, wherein the sensor comprises a sample region configured to come into contact with the bodily fluid.

3. The system of claim 1, wherein the measuring device is an independent module that is removable from the communication terminal, the measuring device further comprises a first port, the communication terminal further comprises a second port configured to mate with the first port, and the measuring device may be repeatedly connected and disconnected to the communication terminal via the first and second ports.

4. The system of claim 1, wherein the measuring device is integral with the housing of the communication terminal.

5. The system of claim 1, wherein the first and second communication interfaces are wireless.

6. The system of claim 1, wherein the historical administration data pertains to insulin administration.

7. The system of claim 1, wherein the substance level measurement values pertain to blood-sugar measurements.

8. The system of claim 1, wherein the processor is further adapted to execute computer implemented instructions to store a particular medical fluid administration setup of an individual person in the memory.

9. A method for administering a medical fluid to a body based on a monitored substance level in a bodily fluid, the method comprising:
    placing the bodily fluid in contact with a sensor on a measuring device disposed in a communication terminal;
    sensing the substance level in the bodily fluid using the sensor of the measuring device;
    communicating the substance level to a processor in the communication terminal;
    determining a medical fluid dosage to be administered to the body by an administration device remote from the communication terminal, the medical fluid dosage determined on the basis of the communicated substance level;
    wirelessly communicating a dosage command from the communication terminal to the administration device;
    administering the medical fluid to the body via the administration device according to the dosage command received from the communication terminal;
    wirelessly communicating information relating to amounts of the medical fluid delivered from the administration device, from the administration device to the communication terminal; and
    storing in a memory the historical medical fluid administration data and the substance level measurement values over time, wherein the memory is part of the communication terminal.

10. The method of claim 9, wherein the measuring device is integral with the communication terminal.

11. The method of claim 9, wherein the historical administration data pertains to insulin administration.

12. The method of claim 9, wherein the substance level measurement values pertain to blood-sugar measurements.

13. The method of claim 9, further comprising storing in the memory a particular medical fluid administration setup of an individual person.

14. The method of claim 9, further comprising reading a fluid administration force and comparing the force to upper and lower threshold values to determine the existence of an occlusion or leak relating to the delivery of the medical fluid from the administration device to the body.

15. A system for administering a medical fluid to a body and for monitoring a substance level in a bodily fluid, the system comprising:
    a computer including a processor, a memory, software, a communication port, and a first communication interface, wherein the memory is configured to store data pertaining to a history of administration of the medical fluid, and wherein the software is configured to provide a graphic of medical fluid administration data as a function of time;
    a measuring device separate and distinct from the computer and including a sensor configured to sense the substance level in the bodily fluid and a transducer adapted to communicate with the communication port, wherein the communication port and the transducer physically mate with each other to be placed in communication with each other; and
    an administration device remote from the computer and including a reservoir adapted to contain the medical fluid, a motor and drive mechanism for displacing the medical fluid from the reservoir into the body, and a second communication interface for communicating with the first communication interface;
    wherein the processor is configured to determine a medical fluid dosage to be delivered on the basis of the measured substance level in the bodily fluid; and
    wherein the first communication interface is configured to wirelessly communicate the dosage to be delivered to the second communication interface of the administration device.

16. The system of claim 15, wherein the measuring device further includes a memory.

17. The system of claim 16, wherein the memory is for storing data pertaining to the substance level sensed by the sensor.

18. The system of claim 15, wherein the computer is a desktop type personal computer.

19. The system of claim 15, wherein the computer is a laptop type personal computer.

20. The system of claim 15, wherein the computer is a hand-held or palm type personal computer.

21. The system of claim 15, wherein the communication port and the transducer physically mate with each other to be placed in communication with each other.

22. The system of claim 21, wherein the transducer is a standard interface card.

23. The system of claim 22, wherein the transducer is a PCMCIA card.

24. The system of claim 15, wherein the first and second communication interfaces are wireless.

25. The system of claim 15, wherein the software is configured for displaying the medical fluid administration data in a spread sheet.

26. The system of claim 15, wherein the administration device further includes a device for monitoring the displacement of the drive mechanism.

27. The system of claim 15, wherein, under normal operating conditions, the computer sends control signals to the motor via the first and second communication interfaces.

28. The system of claim 27, wherein the administration device further includes an emergency control that assumes control of the motor when the control signals from the computer are not available to the motor.

29. The system of claim 15, wherein the computer further comprises a display and the software is configured for graphically displaying an accumulated amount of medical fluid administered, said accumulated amount comprising normal doses and extra dosages caused to be administered by the user.

30. The system of claim 29, wherein the software is further configured for displaying one or more time indications corresponding to medical fluid administrations and the amount of medical fluid associated with each of said administrations over a predetermined period of time.

31. The system of claim 29, wherein the software is further configured for graphically displaying a first axis corresponding to administered amount and a second axis corresponding to a historical time period over which administration has taken place.

32. The system of claim 15, wherein the computer further comprises a display and the display comprises an input area with input fields, each input field associated with a system function, wherein pressing one of the fields activates the respective function.

\* \* \* \* \*

UNITED STATES PATENT AND TRADEMARK OFFICE
CERTIFICATE OF CORRECTION

| | | |
|---|---|---|
| PATENT NO. | : 7,931,613 B2 | Page 1 of 1 |
| APPLICATION NO. | : 10/919030 | |
| DATED | : April 26, 2011 | |
| INVENTOR(S) | : Ulrich Haueter et al. | |

It is certified that error appears in the above-identified patent and that said Letters Patent is hereby corrected as shown below:

Col. 12, Line 53, Claim 1 "memo" should read --memory--.

Signed and Sealed this
Sixth Day of September, 2011

David J. Kappos
*Director of the United States Patent and Trademark Office*